(12) United States Patent
Fritchie et al.

(10) Patent No.: US 8,112,229 B2
(45) Date of Patent: Feb. 7, 2012

(54) METHOD FOR DETERMINING THE ORDER OF EXECUTION OF ASSAYS OF A SAMPLE IN A LABORATORY AUTOMATION SYSTEM

(75) Inventors: Patrick P. Fritchie, Southlake, TX (US); John Curtis Jones, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 842 days.

(21) Appl. No.: 11/809,256

(22) Filed: May 31, 2007

(65) Prior Publication Data

US 2008/0300789 A1    Dec. 4, 2008

(51) Int. Cl.
*G01N 35/00*    (2006.01)
(52) U.S. Cl. ............... 702/19; 700/266; 422/50; 436/43
(58) Field of Classification Search .................... 702/19, 702/22; 422/50–570; 436/43–54; 700/90, 700/214, 228, 231, 245–266; 703/6, 11, 703/12
See application file for complete search history.

(56) References Cited

U.S. PATENT DOCUMENTS

| | | |
|---|---|---|
| 4,533,457 A | 8/1985 | Watanabe |
| 4,619,739 A | 10/1986 | Kanno et al. |
| 4,647,362 A | 3/1987 | Watanabe |
| 4,678,755 A | 7/1987 | Shinohara et al. |
| 4,695,430 A | 9/1987 | Coville et al. |
| 4,797,192 A | 1/1989 | Takiguchi |
| 4,908,320 A | 3/1990 | Zakowski et al. |
| 4,971,913 A | 11/1990 | Manabe et al. |

(Continued)

FOREIGN PATENT DOCUMENTS

EP    0 210 014 A2    1/1987
(Continued)

OTHER PUBLICATIONS

Abbott Laboratories, Architect System, "B12", 6C09, 34-4080/R3, 1-6 (Mar. 2006).

(Continued)

*Primary Examiner* — Lori A. Clow
*Assistant Examiner* — Soren Harward
(74) *Attorney, Agent, or Firm* — Timothy P. Lucier (57) ABSTRACT

A method for arranging assays in an order for execution in a system that employs a plurality of clinical analyzers, typically automated clinical analyzers. The method comprises the steps of (a) prioritizing the order of execution of a number of individual assays in a set of assays for a given sample in a sample container, the priority of an individual assay in the set of assays for the given sample being specified by the sensitivity of the individual assay, wherein there is at least one sample-to-sample carryover contribution from at least one other sample, an assay of the at least one other sample preceding the individual assay of the given sample; (b) comparing the sum of the sample-to-sample carryover contribution(s) from the at least one other sample for at least one assay of the at least one other sample that precedes the individual assay of the given sample to the sensitivity threshold of the individual assay of the given sample; and (c) using this comparison to determine whether to establish an order for the execution of assays for the given sample that includes the individual assay of the given sample or dispense at least a portion of the given sample into at least one additional container in order to carry out the assay.

6 Claims, 4 Drawing Sheets

U.S. PATENT DOCUMENTS

| | | |
|---|---|---|
| 5,025,389 A | 6/1991 | Imai |
| 5,100,622 A | 3/1992 | Mimura et al. |
| 5,282,149 A | 1/1994 | Grandone et al. |
| 5,289,385 A | 2/1994 | Grandone |
| 5,366,896 A | 11/1994 | Margrey et al. |
| 5,380,487 A | 1/1995 | Choperena et al. |
| 5,413,770 A | 5/1995 | Sakaguchi et al. |
| 5,468,646 A | 11/1995 | Mattingly et al. |
| 5,536,049 A | 7/1996 | Coules et al. |
| 5,543,524 A | 8/1996 | Mattingly et al. |
| 5,545,739 A | 8/1996 | Mattingly et al. |
| 5,565,570 A | 10/1996 | Mattingly et al. |
| 5,576,215 A | 11/1996 | Burns et al. |
| 5,669,819 A | 9/1997 | Mattingly et al. |
| 5,682,662 A | 11/1997 | Coules et al. |
| 5,723,795 A | 3/1998 | Merriam |
| 5,730,939 A | 3/1998 | Kurumada et al. |
| 5,776,784 A | 7/1998 | Kegelman et al. |
| 5,783,699 A | 7/1998 | Mattingly et al. |
| 5,795,784 A | 8/1998 | Arnquist et al. |
| 5,856,194 A | 1/1999 | Arnquist et al. |
| 5,859,429 A | 1/1999 | Brown et al. |
| 5,915,282 A | 6/1999 | Merriam et al. |
| 5,915,583 A | 6/1999 | Cloonan et al. |
| 5,938,120 A | 8/1999 | Martin et al. |
| 5,965,828 A | 10/1999 | Merriam |
| 6,022,746 A | 2/2000 | Fritchie et al. |
| 6,063,634 A | 5/2000 | Chomka et al. |
| 6,150,113 A | 11/2000 | Decker et al. |
| 6,153,377 A | 11/2000 | Devare et al. |
| 6,162,645 A | 12/2000 | Lee et al. |
| 6,413,780 B1 | 7/2002 | Bach et al. |
| 6,562,298 B1 | 5/2003 | Arnquist et al. |
| 6,588,625 B2 | 7/2003 | Luoma, II et al. |
| 6,594,588 B1 | 7/2003 | Peden et al. |
| 7,099,802 B2 | 8/2006 | Osaka et al. |
| 7,101,715 B2 | 9/2006 | Devlin et al. |
| 2002/0015665 A1 | 2/2002 | Lindsey et al. |
| 2002/0064884 A1 | 5/2002 | Devlin, Sr. et al. |
| 2002/0147515 A1 | 10/2002 | Fava et al. |
| 2003/0021728 A1 | 1/2003 | Sharpe, Jr. et al. |
| 2003/0040117 A1 | 2/2003 | Devlin, Sr. |
| 2003/0092185 A1 | 5/2003 | Qureshi et al. |
| 2003/0202905 A1 | 10/2003 | Devlin, Sr. et al. |
| 2003/0223472 A1 | 12/2003 | Ravalico et al. |
| 2003/0229475 A1 | 12/2003 | Osaka et al. |
| 2004/0115095 A1 | 6/2004 | Devlin, Sr. et al. |
| 2004/0253146 A1 | 12/2004 | Shiba et al. |
| 2005/0013735 A1 | 1/2005 | Gebrian et al. |
| 2005/0013737 A1 | 1/2005 | Chow et al. |
| 2005/0014285 A1 | 1/2005 | Miller |
| 2005/0037502 A1 | 2/2005 | Miller |
| 2005/0123446 A1 | 6/2005 | Yamazaki et al. |
| 2005/0125186 A1 | 6/2005 | Parvin et al. |
| 2005/0220671 A1 | 10/2005 | Stein et al. |
| 2005/0227360 A1 | 10/2005 | Devlin, Sr. |
| 2005/0279387 A1 | 12/2005 | Blackwell et al. |
| 2006/0148063 A1 | 7/2006 | Fauzzi et al. |
| 2006/0153737 A1 | 7/2006 | Saito et al. |

FOREIGN PATENT DOCUMENTS

| | | |
|---|---|---|
| EP | 0 596 205 A2 | 5/1994 |
| EP | 0 732 591 B1 | 9/1996 |
| EP | 0977039 A2 | 2/2000 |
| EP | 1 355 160 A1 | 10/2003 |
| EP | 1460431 A2 * | 9/2004 |
| EP | 1666888 A2 | 6/2006 |
| WO | 98/45679 | 10/1998 |
| WO | 9845679 | 10/1998 |

OTHER PUBLICATIONS

Abbott Laboratories, Architect, "HBsAg" 1L80, 34-4300/R2, 1-12 (Sep. 2006).

Abbott Laboratories, Architect, "TSH", 6C52, 34-3493/R6, 1-6 (Feb. (2005).

Abbott Laboratories, Clinical Chemistry, "Creatine Kinase," 7D63-20 and 7D63-30, 30-3938/R4, 1-8 (Jan. 2007).

Abbott Laboratories, Clinical Chemistry, "Glucose" 7D66-20, 30-3085/R3, 1-12 (Jan. 2003).

Aeroset System Operations Manual, "Principles of Operation", 200154-101 Section 3, 3-1-3-20 (2004).

Patel, et al., "Sample Cross Contamination Elimination with Minimum Wash Buffer on the ARCHITECT® i2000® Analyzer", Clinical Chemistry, Abstract No. 19, 45(6), Supplement (1999).

Ikeda, et al., "Total Clinical Laboratory Testing System for Laboratory Automation", Hitachi Review, 41(4), 167-172 (1992).

European Patent Office, International Search Report, Aug. 29, 2008.

* cited by examiner

METHOD FOR DETERMINING THE ORDER OF EXECUTION OF ASSAYS OF A SAMPLE IN A LABORATORY AUTOMATION SYSTEM

BACKGROUND OF THE INVENTION

1. Field of the Invention

This invention relates to sample-to-sample carryover in an automated clinical analyzer, and, more particularly, addressing the problem of sample-to-sample carryover in an automated clinical analyzer by improving the order of execution of assays in a set of assays.

2. Discussion of the Art

A laboratory automation system integrates at least one clinical analyzer with the other components of the system for the purpose of automating the delivery of samples between the at least one clinical analyzer and those other components of the system. The at least one clinical analyzer is typically an automated clinical analyzer. A laboratory automation system can comprise, and preferably does comprise, a plurality of automated clinical analyzers.

It is known that whenever a sample probe of an automated clinical analyzer aspirates a given sample or a portion thereof from a sample container, the sample probe has the potential for contaminating the sample with a small portion of a different sample that had been aspirated previously. This mode of contamination is typically referred to as carryover, more particularly, sample-to-sample carryover. Automated clinical analyzers employ aggressive techniques for washing sample probes, special cleaning solutions for washing sample probes, and large volumes of probe cleaning solutions to minimize this type of carryover. See, for example, United States Patent Application Publication No. 2003/0223472 A1 and United States Patent Application Publication No. 2005/0279387 A1, both of which are incorporated herein by reference. However, because in most cases a sample probe can never be completely cleaned, i.e., to a level at which sample-to-sample carryover is completely eliminated, techniques for cleaning sample probes merely reduce carryover to an acceptable level, as determined by the operator of the automated clinical analyzer or on the basis of the sensitivity of the assay. It is also known that a given assay has a sensitivity threshold. Sensitivity threshold refers to the minimum concentration of analyte in a sample that can be detected or measured or both. Depending on the sensitivity threshold of a particular assay, this sample-to-sample carryover can adversely affect results.

Currently, to avoid the effects of contamination of a sample by sample-to-sample carryover by the sample probe of an automated clinical analyzer in a laboratory automation system, a portion of the sample is aspirated from the original sample container and dispensed into an additional sample container, and a disposable tip is applied to the sample probe prior to aspirating the sample from the additional sample container. This sample transfer step increases costs, because additional sample containers and identifying indicia therefor, such as, for example, barcodes, are required. More importantly, the transfer step delays reporting of results, which could adversely affect the care of a patient. In addition, although disposable tips eliminate sample-to-sample carryover completely, the use of disposable tips is much more costly than merely washing the reusable sample probe between dispensing steps.

If the sample is a STAT sample (i.e., Short Turn Around Time sample) and results from more than one clinical analyzer are required quickly, it may be more expedient to aspirate at least one portion of the sample from the original sample container and dispense that at least one portion into at least one additional sample container, each additional sample container having its own position in the order for execution of an assay. However, additional costs will be incurred for the additional sample containers, additional labels for the additional sample containers, etc.

U.S. Pat. No. 4,971,913 discloses a method of controlling a reagent delivery system for delivering a plurality of different reagents into successive sample-containing reaction vessels in an automatic chemical analyzer for measurement of corresponding tests specimens in a plurality of test items. The method comprises the steps of:

preparing at least one reagent delivery device, the number of which is smaller than that of the reagents of differing kinds;

storing in memory means information representing a predetermined relation between the test items with respect to the influence of contamination between the reagents upon a measurement; and controlling the operation of the reagent delivery device in accordance with the predetermined relation stored in the memory means in such a manner that the measurement is not affected by the contamination between the reagents.

This patent deals solely with contamination by reagents.

WO 98/45679 discloses a method and apparatus for optimizing the sequence of assays on an automated random access instrument so as to reduce reagent cross-contamination problems. A common vehicle for reagent cross-contamination is the reagent probe surface, which transfers reagents for the various tests. When a plurality of assays are run on a single sample, an initial best path (order of assays) is identified, after which the iterative process of looking for a better alternative begins. This process involves the application of a knowledge base concerning relationships associated with random access cross-contamination, to search the state space. This reference, too, deals with contamination by reagents.

It would be desirable to develop a method whereby the order of execution of assays is integrated with the workflow of the laboratory, additional costs resulting from the use of additional sample containers are minimized, and acceptable response times for STAT samples are still maintained.

SUMMARY OF THE INVENTION

In one aspect, this invention provides a method for arranging assays in an order for execution in a system that employs at least one clinical analyzer, typically an automated clinical analyzer. The method comprises the steps of:

(a) prioritizing the order of execution of a number of individual assays in a set of assays for a given sample in an original sample container, the priority of an individual assay in the set of assays for the given sample being specified by the sensitivity of the individual assay, wherein there is at least one sample-to-sample carryover contribution from at least one other sample, an assay of the at least one other sample preceding the individual assay of the given sample;

(b) calculating the sum of the sample-to-sample carryover contribution(s) from the at least one other sample for the at least one assay of the at least one other sample that precedes the individual assay of the given sample;

(c) comparing the sum calculated in step (b) to the sensitivity threshold of the individual assay of the given sample; and (d) if the sum calculated in step (b) is less than the sensitivity threshold of the individual assay of the given sample, establishing an order for the execution of assays for the given sample that includes the individual assay of the given sample, but if the sum calculated in step (b) is greater than the sensitivity threshold of the individual assay of the given sample, aspirating at least one portion of the given sample from the original sample container and dispensing that at least one portion into at least one additional sample container, the at least one portion of the given sample dispensed into the at least one additional sample container to be used to carry out the individual assay of the given sample.

By ordering that the assays for a given sample in the original sample container be carried out in descending order of sensitivity, the quantity of sample containers required for performing a set of assays for the given sample can be minimized.

In another aspect of the invention, after the order for execution of assays for a given sample is established, the method further includes the step of determining the sensitivity threshold for rerunning an individual assay or performing a reflex test of an individual assay, depending on the initial results of the individual assay. After this step for determining for the sensitivity threshold is complete, the method includes the step of determining if a waiting period is preferred. A waiting period can be useful if an assay having a high degree of sensitivity is to be rerun after the assay is run initially. Because of the desire to avoid sample-to-sample carryover, the use of a waiting period can substantially reduce the adverse effects of sample-to-sample carryover. If a waiting period is not required, the order for execution of assays is established and the set of assays can be carried out. If a waiting period is required, the method includes the step of determining whether a STAT sample is to be analyzed. If a STAT sample is to be analyzed, at least one portion of the sample is aspirated from the original sample container and that at least one portion is dispensed into at least one additional sample container, the portion of the sample dispensed into the at least one additional sample container being used to carry out the assay of the STAT sample. If an assay of a STAT sample is not to be performed, a waiting period for awaiting valid results can be established, with no rerunning of an assay or performing of a reflex test being required.

The method, or algorithm, for arranging the order of execution of assays in a laboratory automation system will minimize the need for transferring portion(s) of the sample from the original sample container to additional sample container(s). As a result, the number of operations typically performed with disposable tips on a sample probe will be greatly reduced, thereby reducing the costs of disposable items, and the need for additional sample containers (e.g., sample tubes) and container-identifying indicia (e.g., barcodes) would also be eliminated, thereby further reducing the costs of disposable items. The results of these savings would lead to lower cost per assay or test for a laboratory, and reduced time for reporting results to the doctor and the patient. The method, or algorithm, for arranging the order of execution of assays in a laboratory automation system reduces the potential for interference caused by sample-to-sample carryover into a given sample, thereby resulting in maintaining the integrity of the given sample and the accuracy and precision of the test results for the given sample.

DETAILED DESCRIPTION

As used herein, the expression "laboratory automation system" means a system designed to automate the processing of samples prior to, during, and subsequent to analyzing the samples. The processing includes handling of the samples, moving the samples from a clinical analyzer to other components of the system, and storing of the samples.

As used herein, the term "sample" means a material suspected of containing an analyte. The sample can be used directly as obtained from the source in an assay or following a pretreatment to modify the character of the sample before undergoing an assay. The sample can be derived from any biological source, such as, for example, a physiological fluid, including, but not limited to, blood, saliva, ocular lens fluid, cerebral spinal fluid, sweat, urine, milk, ascites fluid, mucous, synovial fluid, peritoneal fluid, amniotic fluid, or the like. The sample can be pretreated prior to use, such as, for example, preparing plasma from blood, diluting viscous fluids, or the like. Methods of treatment can involve filtration, distillation, concentration, inactivation of interfering components, and the addition of reagents. Besides physiological fluids, other liquid samples can be used, such as, for example, water, food products, and the like. In addition a solid material suspected of containing the analyte can be used as the sample. As used herein, the term "analyte" refers to the compound or composition to be detected or measured.

As used herein, the expression "sample-to-sample carryover" means the residue of a sample that is carried on the surface of a sample probe from the contact of the sample probe to a first sample in a first container to the contact of the sample probe to a second sample in a second container. The major problem with sample-to-sample carryover is that in the situation of a highly sensitive assay, the analyte in a given sample would be carried over to a second sample, with the result that an assay of the second sample could very likely lead to an assay of the second sample yielding a false positive result. Sample-to-sample carryover accumulates when a given sample is aspirated at different clinical analyzers, whereat other samples have been aspirated, or when another sample is aspirated between consecutive aspirations of the given sample at the same clinical analyzer. For example, if a given sample, e.g., sample A, is aspirated four times by one clinical analyzer for four different assays, then the sample-to-sample carryover contribution from that clinical analyzer is only counted once. If, however, the given sample, e.g., sample A, is aspirated one time by four different clinical analyzers, then the sample-to-sample carryover contribution from each of the four clinical analyzer is accumulated in the sample A. In the situation of a rerun assay of a given sample, e.g., sample A, while sample A is being held, if other samples, e.g., sample B, sample C, and sample D, were aspirated at the same clinical analyzer between the initial aspiration of sample A and the aspiration of sample A for the rerun assay, then the sample-to-sample carryover contributions from the samples B, C, and D from the clinical analyzer would be counted in the sample A.

As used herein, the term "sensitivity" means the lowest concentration of an analyte that can be detected in a sample.

As used herein the expression "sensitivity threshold" means the concentration below which the lowest concentration of an analyte that cannot be detected in a sample. In relative terms, if the concentration of an analyte in a sample is low, the assay must have a high sensitivity to detect the analyte; if the concentration of an analyte in a sample is high, the assay can have a low sensitivity to detect the analyte.

As used herein, the expression "individual assay" means a particular assay of a set of or a plurality of assays for which the presence or concentration or both presence and concentration of an analyte is determined. As used herein, the expressions "set of assays" and "plurality of assays" mean the group of assays of which the individual assay is a member that are to be performed on a sample. As used herein, the term "rerun assay" refers to the performing of an individual assay from a given sample at least a second time, wherein that individual assay has been performed once for the given sample. The option to perform a rerun assay can be automatic, for example when the system has detected a failure on an analyzer; alternatively, a rerun assay can be started manually, if the technical person is unsure about the accuracy of certain results and/or wishes to have them confirmed. As used herein, the term "reflex test" refers to the performing of a subsequent assay that is called for after the results of a preceding assay are obtained. For example, if an individual assay indicates that the concentration of TSH (thyroid stimulating hormone) is high, then a reflex assay for FT4 (free thyroxine) may be called for. Assays selected by an operator may specify the use of operator-defined ranges to automatically run a different assay than the assay originally selected.

As used herein, the expression "waiting period" means the extent of time wherein a sample container is held, to prevent additional aspirations therefrom, until the results from the assay in progress are reported. If the results are deemed to be valid, the sample container can be released to other clinical analyzers, if such other clinical analyzers are present. If the results indicate that the assay should be rerun or that a reflex test should be performed, the sample container is first returned to the clinical analyzer on which the assay was initially performed, and then subsequently released to other clinical analyzers, if such other clinical analyzers are present.

As used herein, the expression "original sample container" means the sample container from which the sample is aspirated for either an individual assay or for transfer to an another sample container from which the sample can be aspirated for an individual assay.

As used herein, the expression "and/or" is used to indicate that either "and" or "or" may be used to connect words, phrases, or clauses. The use of the symbol "(s)" following a word means one or more, depending upon the context.

Laboratory automation systems comprise at least one type of clinical analyzer. Laboratory automation systems can comprise two or more different types of clinical analyzers. Furthermore, the at least one type of clinical analyzer is typically an automated clinical analyzer. One type of automated clinical analyzer can be used to carry out immunoassays. Representative examples of automated immunoassay analyzers suitable for use in this invention include, but are not limited to, those described in U.S. Pat. Nos. 5,795,784; 5,856,194; 6,413,780; 6,562,298, all of which are incorporated herein by reference. Another type of automated clinical analyzer can be used to carry out clinical chemistry assays. Representative examples of automated clinical chemistry analyzers suitable for use in this invention include, but are not limited to, those described in U.S. Pat. Nos. 4,647,362; 4,678,755, both of which are incorporated herein by reference. Some automated clinical analyzers can be used to carry out both immunoassays and clinical chemistry assays.

Figure 1:
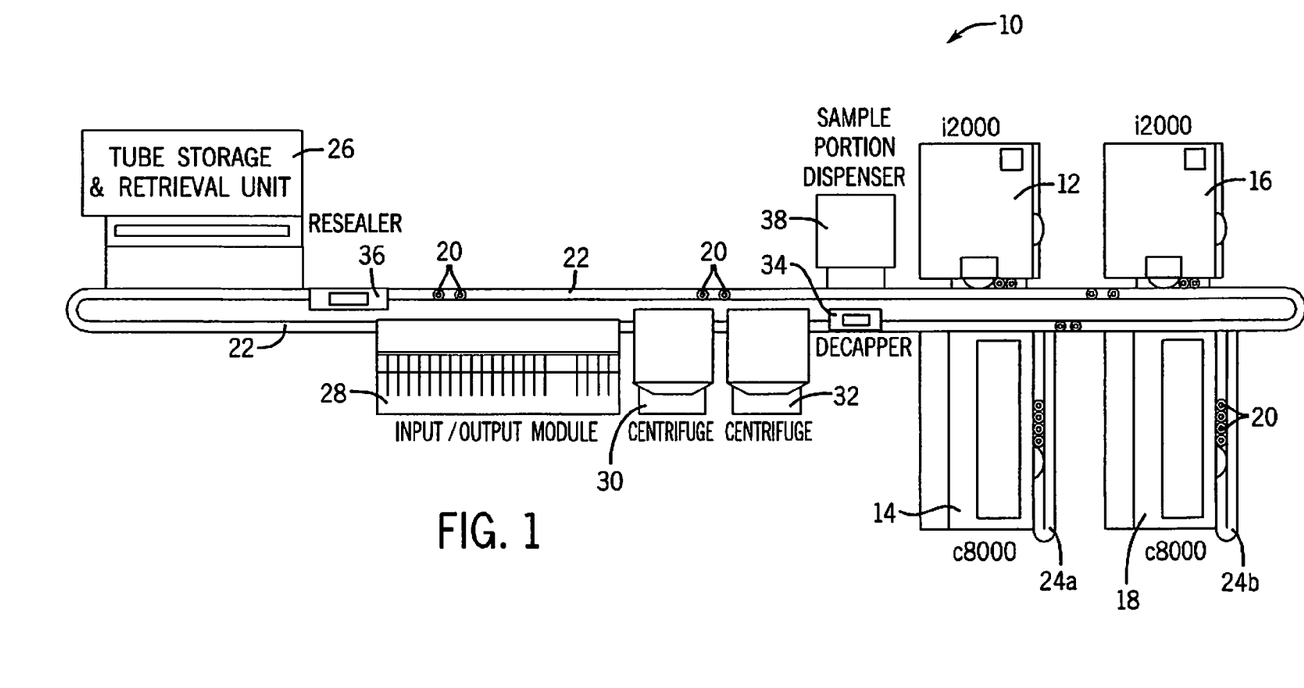
FIG. 1 is a schematic view of a laboratory automations system.
Figure 3:
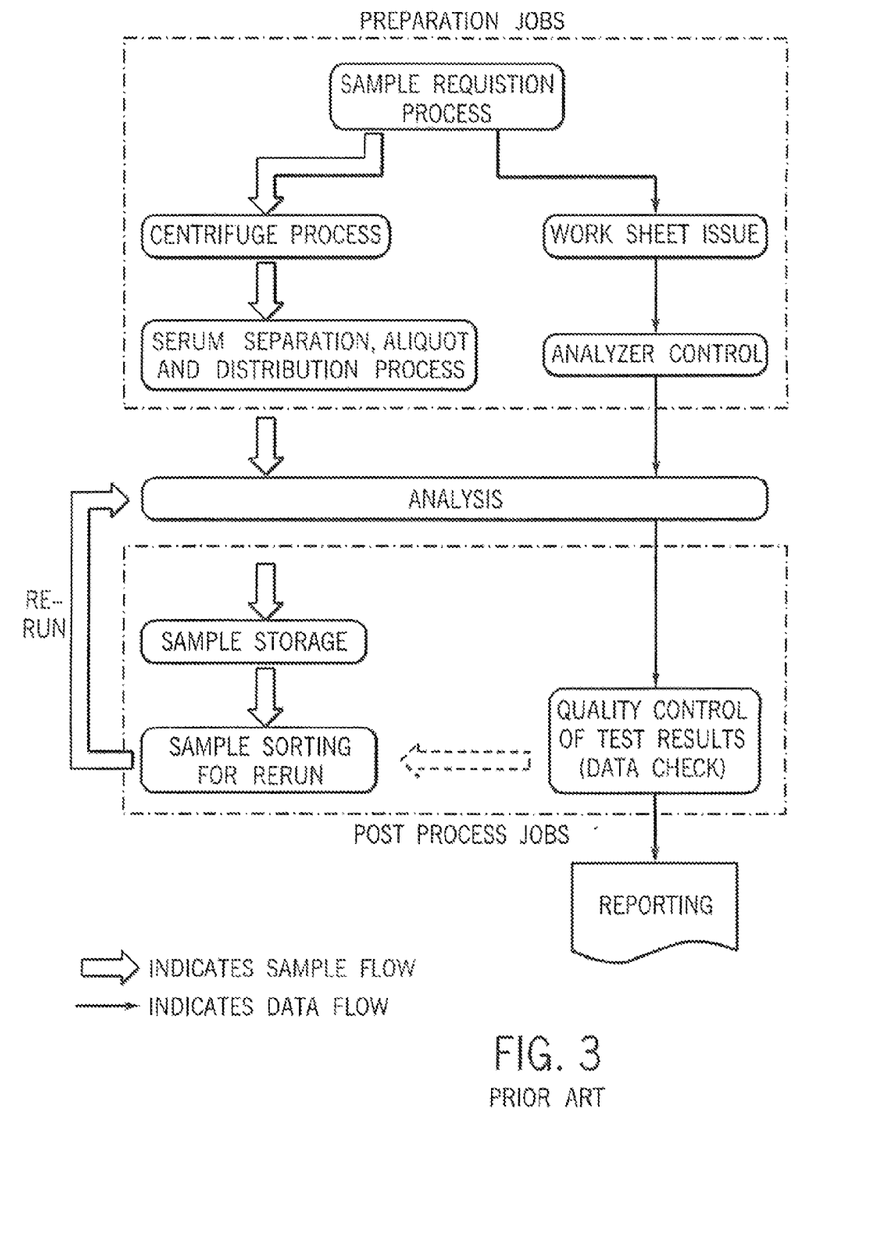
FIG. 3 is a flow chart illustrating a prior art laboratory automation system.
Figure 4:
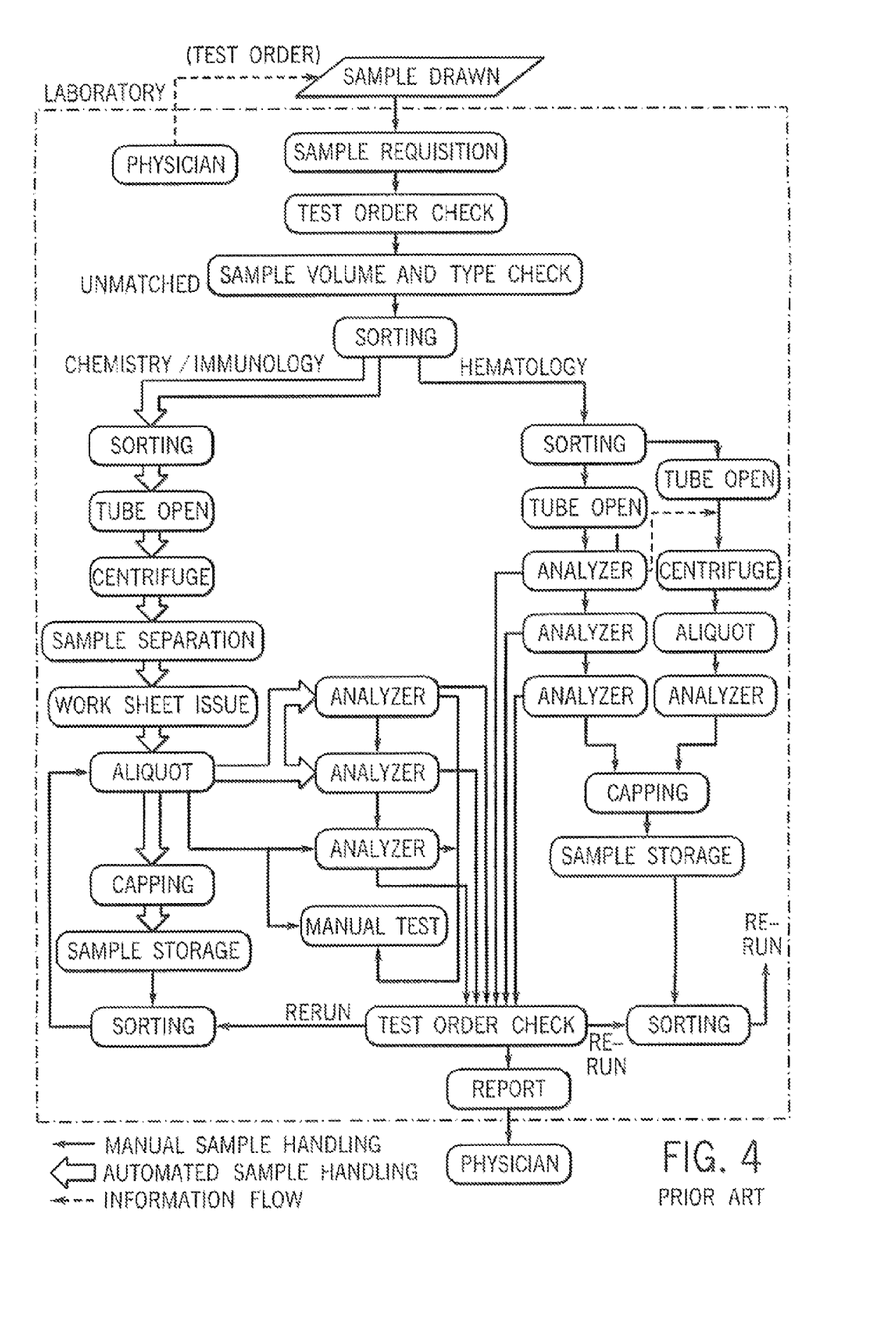
FIG. 4 is a flow chart illustrating a prior art laboratory automation system.

FIG. 1 illustrates a laboratory automation system 10 that comprises a first automated immunoassay analyzer 12, a first automated clinical chemistry analyzer 14, a second automated immunoassay analyzer 16, and a second automated clinical chemistry analyzer 18. Each of the automated analyzers 12, 14, 16, and 18 has at least one probe (not shown) that is capable of aspirating a sample from a sample container 20. In FIG. 1, a total of twenty (20) sample containers are shown. It is these probes that cause the sample-to-sample carryover problem addressed herein. A track system upon which a sample container 20 can move comprises a main track 22 and spur tracks 24a and 24b. The spur track 24a enables a sample container to be moved from the main track 22 to the automated clinical chemistry analyzer 14; the spur track 24b enables a sample container to be moved from the main track 22 to the automated clinical chemistry analyzer 18. In the system 10 shown in FIG. 1, other components that are typically included in a laboratory automation system include, but are not limited to, a tube storage and retrieval unit 26 for storing samples upon which a set of assays has been performed and an input/output module 28 for (a) introducing sample containers 20 to the laboratory automation system 10 and (b) removing sample containers 20 from the laboratory automation system 10. Also shown in FIG. 1 are a first centrifuge system 30 and a second centrifuge system 32 for separating serum from cells in a sample of blood, a decapper 34 for removing caps from sample containers 20, typically caps from sample tubes, and a resealer 36 for sealing the sample container after completion of analytical testing. Still further shown in FIG. 1 is a sample portion dispenser 38. The function of the sample portion dispenser 38 is to aspirate at least one portion of a sample from an original container and dispense that at least one portion of the sample into at least one additional sample container. The at least one additional sample container can be used when an assay is performed on a STAT sample or when the value of cumulative sample-to-sample carryover contributions exceed the sensitivity threshold of an assay that was expected to be performed on the sample in the original sample container. Sample portion dispensers 38 suitable for use in the laboratory automation system 10 described herein are commercially available and are well known to those having ordinary skill in the art. Not shown in FIG. 1, but necessarily present in a laboratory automation system, is a control unit for handling information in the laboratory automation system 10 and for providing instructions to the laboratory information system 10 for operating the various components of the system. The control unit can be a computer, e.g., a personal computer. Additional discussion of a simple laboratory automation system can be found in Ikeda et al., "Total Clinical Laboratory Testing System for Laboratory Automation", Hitachi Review, Vol. 41 (1992) No. 4, pages 167-172, incorporated herein by reference, hereinafter "Ikeda et al." FIG. 3 shows the overall workflow. Hitachi targeted several units for single functions, such as centrifuge, tube opening, aliquot, and transportation, to be able to build up a total system from an assortment of single units. The system configurations should be easy to change, depending on each customer situation such as workload volume, budget, and laboratory layout. The target units are decided based on the work-flow analysis of FIG. 5. FIG. 3 of Ikeda et al. is reproduced as FIG. 3 herein. FIG. 5 of Ikeda et al. is reproduced as FIG. 4 herein. Examples of automated immunoassay analyzers, automated clinical chemistry analyzers, tube storage and retrieval units, input/output modules, centrifuge systems, decappers, and resealers are well-known to those of ordinary skill in the art and are readily commercially available from numerous sources.

Figure 2:
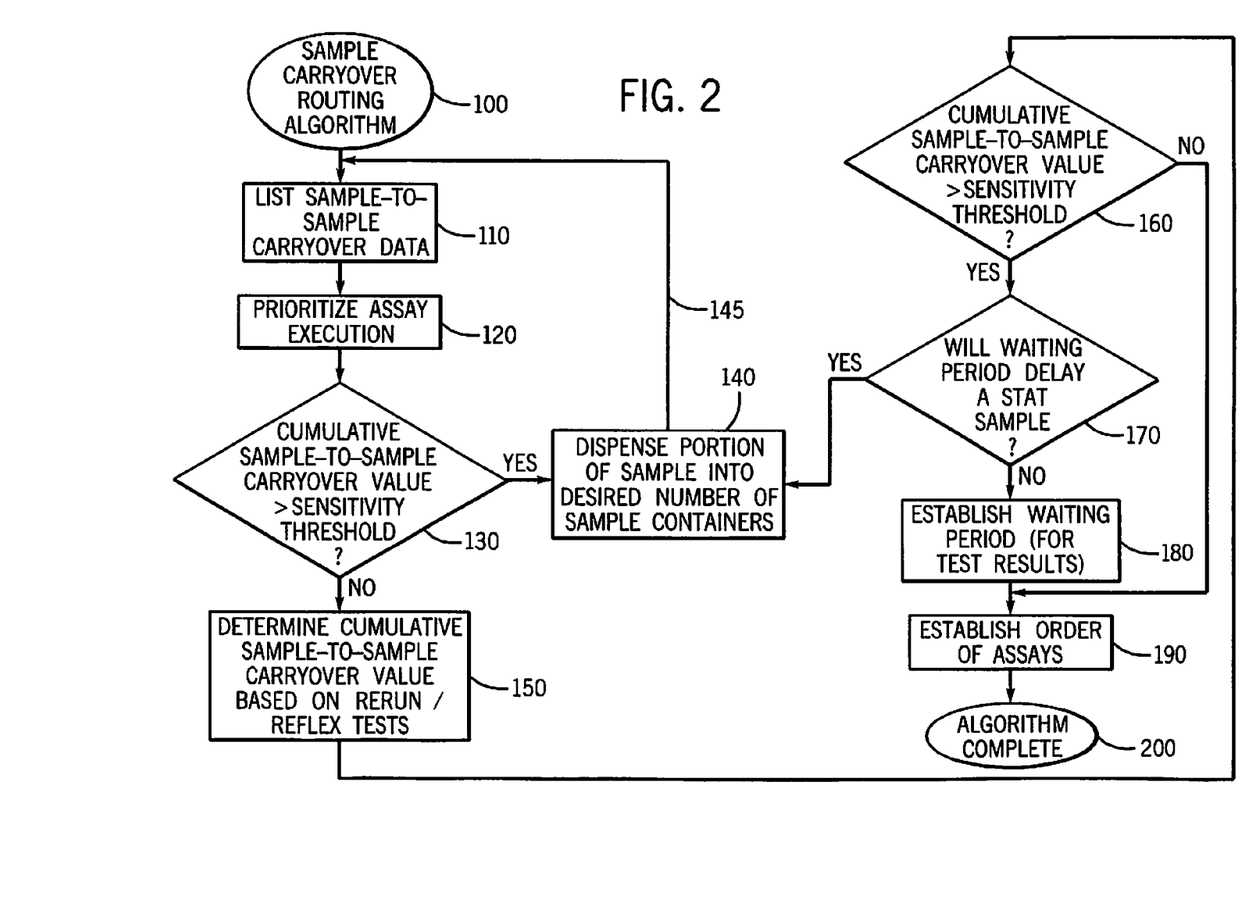
FIG. 2 is a flow chart illustrating a method, or algorithm, for arranging the order of the execution of assays suitable for reducing the effects of sample-to-sample carryover.

FIG. 2 illustrates an algorithm 100 suitable for use in carrying out the method described herein. Step 110 of the flow chart shown in FIG. 2 provides data of the type shown in TABLE 1. TABLE 1 illustrates hypothetical carryover parameters for a laboratory automation system that can employ five clinical analyzers.

TABLE 1

| Analyzer | Sample-to-sample carryover for a single aspiration step |
|---|---|
| Immunoassay analyzer no. 1 (IA-1) | 0.1 ppm ($1 \times 10^{-7}$) |
| Clinical chemistry analyzer no. 1 (CC-1) | 0.1 ppm ($1 \times 10^{-7}$) |
| Immunoassay analyzer no. 2 (IA-2) | 0.1 ppm ($1 \times 10^{-7}$) |
| Immunoassay analyzer no. 3 (IA-3) | 0.1 ppm ($1 \times 10^{-7}$) |
| Combined immunoassay analyzer and clinical chemistry analyzer no. 1 (IA/CC-1) | 0.1 ppm ($1 \times 10^{-7}$) |

The data shown in TABLE 1 are frequently set forth in operators' manuals provided by manufacturers of analyzers. The data can be derived by observing a tracking material, such as, for example, a radioactive tracer or a dye. Step 110 of the flow chart also utilizes data of the type shown in TABLE 2. The data shown in TABLE 2 are typically developed by assay developers and are typically set forth in package inserts of assay kits.

In step 120 of the algorithm 100, the order of execution of assays is prioritized in accordance with the carryover data from step 110. In general, a given sample is utilized for one (1) or two (2) immunoassays and for from about eight (8) to about ten (10) clinical chemistry assays. TABLE 2 illustrates typical sensitivity thresholds for a few assays.

TABLE 2

| Analyte of the assay | Sensitivity threshold |
|---|---|
| Assay no. 1 (A-1) | 100 ppm ($1 \times 10^{-4}$) |
| Assay no. 2 (A-2) | 150 ppm ($1.5 \times 10^{-4}$) |
| Assay no. 3 (A-3) | 10 ppm ($1 \times 10^{-5}$) |
| Assay no. 4 (A-4) | 0.5 ppm ($5 \times 10^{-7}$) |
| Assay no. 5 (A-5) | 0.1 ppm ($1 \times 10^{-7}$) |

The step 120 of the algorithm 100 involves prioritizing execution of a plurality of assays as a function of sample-to-sample carryover. It is possible that sample-to-sample carryover from a first (prior) sample used in a previous assay can impart to a second (subsequent) sample a concentration value of an analyte that exceeds the sensitivity threshold of an individual assay to thereby give a false result in the individual assay. Therefore, it is necessary to track the cumulative sample-to-sample carryover, i.e., carryover resulting from the aspiration and dispensing of each sample, so that the order of the assays to be carried out can be arranged to maintain the value of cumulative sample-to-sample carryover below a specified level, so that the individual assay can detect and/or measure the concentration of the analyte in the sample.

An initial determination of priority, i.e., determination of priority without regard to rerun assays and reflex tests, involves introducing the sensitivities of the assays of a particular set of assays to be run for a given sample into a computer, e.g., a personal computer, and introducing the sample-to-sample carryover values for the automated clinical analyzer(s) to be used for carrying out the assays into the computer. In order to effectively perform the algorithm for ordering the execution of assays, the sensitivities of each individual assay of a plurality of assays are listed in order of sensitivity from the most sensitive assay (highest sensitivity) to the least sensitive assay (lowest sensitivity). The sample-to-sample carryover contributions brought about by the sample probe(s) of the particular clinical analyzer(s) to be used for carrying out the aforementioned set of assays are listed in the same order as are the aforementioned sensitivities. For example, if an individual assay "x" has the highest sensitivity, assay "x" will be listed first; if an individual assay "y" has the next highest sensitivity, assay "y" will be listed next. The sample-to-sample carryover contribution from the clinical analyzer on which assay "x" will be performed is listed first; the sample-to-sample carryover contribution from the clinical analyzer on which assay "y" will be performed is listed next. Such a listing of particular assays and sample-to-sample carryover contributions from the clinical analyzer(s) on which the particular assays will be performed is completed for the total number of assays to be run in a set of assays, with each subsequent assay being less sensitive than the preceding assay. An example of such a listing is shown in TABLE 3.

The value of the cumulative sample-to-sample carryover contributions from the clinical analyzer(s) listed are determined by adding the sample-to-sample carryover contribution from the first clinical analyzer to the sample-to-sample carryover contribution from the second clinical analyzer to obtain the first value of cumulated sample-to-sample carryover contribution. In similar manner, the sample-to-sample carryover contribution from the third clinical analyzer is added the first value of cumulated sample-to-sample carryover contribution to obtain the second value of cumulative sample-to-sample carryover contribution. The cumulative sample-to-sample carryover contribution from each subsequent clinical analyzer is calculated in a similar manner.

The following equation summarizes the calculation of the values for the cumulative sample-to-sample carryover contribution for each clinical analyzer:

$$CSSC_n = SSC_1 + \ldots + SSC_n$$

Where CSSC represents cumulative sample-to-sample carryover contribution from a clinical analyzer;
SSC represents sample-to-sample carryover contribution from a clinical analyzer;
n represents the number of different clinical analyzers that contact a given sample.

It should be noted that the particular assays listed in TABLE 3 call for only two different clinical analyzers (IA-2 and IA-3). Additional clinical analyzers can be used in the method described herein. As indicated previously, a single clinical analyzer can provide multiple sample-to-sample carryover contributions to a given sample, if there exists a situation in which the given sample can be contaminated by sample-to-sample carryover contributions from other samples.

In step 130, i.e., a comparison step, the sum of the individual sample-to-sample carryover contributions in the fifth column (from the left) of TABLE 3, is compared with the assay sensitivity data in the second column (from the left) of TABLE 3, which table illustrates the prioritization of a set of assays for a given sample and calculation of the values of cumulative sample-to-sample carryover contributions in order to determine an acceptable order for executing assays from a sample in a sample container. Assays A-1, A-2, A-3, A-4, and A-5 are aspirated from the same sample container.

TABLE 3

| Order of assay from most sensitive to least sensitive | Sample-to-sample carryover contribution of each analyzer | | Cumulative sample-to-sample carryover contribution from the analyzers listed/requirement of additional sample container | |
|---|---|---|---|---|
| A-5 0.1 ppm $(1 \times 10^-)^7$ | IA-3 | 0.1 ppm $(1 \times 10^{-7})$ | 0 | Additional sample container not required |
| A-4 0.5 ppm $(5 \times 10^{-7})$ | IA-3 | 0.1 ppm $(1 \times 10^{-7})$ | 0.1 ppm $(1 \times 10^{-7})$ | Additional sample container not required |
| A-3 10 ppm $(1 \times 10^{-5})$ | IA-3 | 0.1 ppm $(1 \times 10^{-7})$ | 0.1 ppm $(1 \times 10^{-7})$ | Additional sample container not required |
| A-1 100 ppm $(1 \times 10^{-4})$ | IA-2 | 0.1 ppm $(1 \times 10^{-7})$ | 0.2 ppm $(2 \times 10^{-7})$ | Additional sample container not required |
| A-2 150 ppm $(1.5 \times 10^{-4})$ | IA-2 | 0.1 ppm $(1 \times 10^{-7})$ | 0.2 ppm $(2 \times 10^{-7})$ | Additional sample container not required |

As shown in TABLE 3, the value of cumulative sample-to-sample carryover contribution for each aspiration of the sample never exceeds the sensitivity threshold of an individual assay when each of the plurality of assays is performed in the order shown in the first column (from the left) of TABLE 3. Thus, the arrangement of the execution of these assays by most sensitive to least sensitive can be used for ordering the execution of assays. This arrangement can be used by a laboratory automation system to automatically move a sample container, or by an operator to manually move a sample container, if manual operation is desired.

Referring again to step 130, if, for an individual assay, the comparison indicates that the value of the cumulative sample-to-sample carryover contribution is greater than the sensitivity threshold for the individual assay, at least one portion of the sample is aspirated from the original sample container and that at least one portion is dispensed into at least one additional sample container, according to step 140. The algorithm 100 can also be designed to include subroutines to indicate the precise number of additional sample containers, and labels, that are required to carry out step 140. The number of additional sample containers required is entered and the algorithm 100 is restarted, as shown by the path 145 in the process flow diagram of FIG. 2.

Referring once again to step 130, if, for an individual assay, the comparison indicates that the value of the cumulative sample-to-sample carryover contribution is less than the sensitivity threshold for the individual assay, the value of the cumulative sample-to-sample carryover contribution is determined based on a selected number of rerun assays and/or reflex tests. The number of rerun assays and/or reflex tests can be determined by the assay developer. A rerun assay or reflex test may be required when a result appears to be suspicious, such as, for example, when the result is inordinately high, inordinately low, of otherwise unexpected. The rerun assay/reflex test determination step 150 utilizes the same type of data that is provided in TABLES 1 and 2. In order to effectively perform step 150 of the algorithm 100, the sensitivities of each individual rerun assay and/or reflex test of a plurality of assays are listed in order of sensitivity from the most sensitive assay (highest sensitivity) to the least sensitive assay (lowest sensitivity), but are listed after the listing of the initial assays to be carried out on a sample. This manner of listing is desirable because the rerun assay and/or reflex test typically awaits the results of the initial assays, in order for the results of the initial assays to provide an indication that either such a rerun assay and/or reflex test is required or desired or such a rerun assay and/or reflex test is neither required nor desired. The sample-to-sample carryover contributions brought about by the sample probe(s) of the particular clinical analyzer(s) to be used for carrying out the aforementioned set of assays are listed in the same order as are the aforementioned sensitivities. For example, if an individual assay "x" has the highest sensitivity, assay "x" will be listed first; if an individual assay "y" has the next highest sensitivity, assay "y" will be listed next. The clinical analyzer on which assay "x" will be performed is listed first; the clinical analyzer on which assay "y" will be performed is listed next. Such a listing of particular assays and sample-to-sample carryover contributions from the clinical analyzers on which the particular assays will be performed is completed for the total number of assays to be run in a set of assays, with each subsequent assay being less sensitive than the preceding assay, except for the rerun assays and/or reflex tests. An example of such a listing is shown in TABLE 4. However, the listing in TABLE 4 results in an ERROR MESSAGE, which will be described in further detail later.

The value of the cumulative sample-to-sample carryover contribution from the clinical analyzer(s) listed are determined by adding the sample-to-sample carryover contribution from the first clinical analyzer to the sample-to-sample carryover contribution from the second clinical analyzer to obtain the first value of cumulated sample-to-sample carryover contribution. In similar manner, the sample-to-sample carryover contribution from the third clinical analyzer is added the first value of cumulated sample-to-sample carryover contribution to obtain the second value of cumulative sample-to-sample carryover contribution. The cumulative sample-to-sample carryover contribution from each subsequent clinical analyzer is calculated in a similar manner.

The following equation summarizes the calculation of the values for the cumulative sample-to-sample carryover contribution from each clinical analyzer:

$$CSSC_n = SSC_1 + \ldots + SSC_n$$

Where CSSC represents cumulative sample-to-sample carryover contribution from a clinical analyzer;
SSC represents sample-to-sample carryover contribution from a clinical analyzer;
n represents the number of different clinical analyzers that contact a given sample.

It should be noted that the particular assays listed in TABLE 4 call for only two different clinical analyzers (IA-2 and IA-3). Additional clinical analyzers can be used in the method described herein. As indicated previously, a single clinical analyzer can provide multiple sample-to-sample carryover contributions to a given sample, if there exists a situation in which the given sample can be At step 160, i.e., a comparison step, the data in the fifth column (from the left) of TABLE 4 are compared with the data in the second column (from the left) of TABLE 4 to determine whether the rerun assay or the reflex test can be carried out. TABLE 4 illustrates the prioritization of a set of assays for a given sample and calculation of the values of cumulative sample-to-sample carryover contributions in order to determine an acceptable order for executing assays from a sample in a sample container. Assays A-1, A-2, A-3, A-4, and A-5 are aspirated from the same sample container. In TABLE 4, the assay A-5 is run a second time as a rerun assay.

The difference between the prioritization of a set of assays comprising a rerun assay and/or a reflex test and the prioritization of a set of assays that does not call for a rerun assay and/or a reflex test depends upon whether assays are likely to be in need of a rerun assay or a reflex test. However, if the sensitivity threshold of a given assay is high, e.g., from about 100 ppm to about 150 ppm or higher, the amount of sample-to-sample carryover may not be critical. If, for a given rerun assay or reflex test, the value of cumulative sample-to-sample carryover contribution for the rerun assay or reflex test does not exceed the sensitivity threshold of the rerun assay or reflex test when each of the plurality of assays is performed in the order shown in the first column (from the left) of TABLE 4, an order for the execution of assays is then established, and the algorithm is complete. Thus, the arrangement of the execution of these assays by most sensitive to least sensitive can be used for ordering the execution of assays. This arrangement can be used by a laboratory automation system to automatically move a sample container, or by an operator to manually move a sample container, if manual operation is desired. However, TABLE 4 illustrates an ERROR MESSAGE, because the value of the cumulative sample-to-sample carryover contribution exceeds the sensitivity threshold of an individual assay, i.e., the rerun assay A-5.

TABLE 4

| Order of assay from most sensitive to least sensitive | Sample-to-sample carryover contribution of each analyzer | | Cumulative sample-to-sample carryover contribution from the analyzers listed/requirement of additional sample container | |
| --- | --- | --- | --- | --- |
| A-5 | 0.1 ppm ($1 \times 10^{-7}$) | IA-3 | 0.1 ppm ($1 \times 10^{-7}$) | 0 | Additional sample container not required |
| A-4 | 0.5 ppm ($5 \times 10^{-7}$) | IA-3 | 0.1 ppm ($1 \times 10^{-7}$) | 0.1 ppm ($1 \times 10^{-7}$) | Additional sample container not required |
| A-3 | 10 ppm ($1 \times 10^{-5}$) | IA-3 | 0.1 ppm ($1 \times 10^{-7}$) | 0.1 ppm ($1 \times 10^{-7}$) | Additional sample container not required |
| A-1 | 100 ppm ($1 \times 10^{-4}$) | IA-2 | 0.1 ppm ($1 \times 10^{-7}$) | 0.2 ppm ($2 \times 10^{-7}$) | Additional sample container not required |
| A-2 | 150 ppm ($1.5 \times 10^{-4}$) | IA-2 | 0.1 ppm ($1 \times 10^{-7}$) | 0.2 ppm ($2 \times 10^{-7}$) | Additional sample container not required |
| Rerun A-5 | 0.1 ppm ($1 \times 10^{-7}$) | IA-3 | 0.1 ppm ($1 \times 10^{-7}$) | 0.3 ppm ($3 \times 10^{-7}$) | ERROR MESSAGE |

The error indicated could also occur on an initial ordering of the execution of assays, if the value of cumulative sample-to-sample carryover contributions exceeds the sensitivity threshold of an individual assay. In either case, an ERROR MESSAGE would be indicated, and there are at least two techniques for addressing this ERROR MESSAGE.

If, for a given rerun assay or reflex test, the comparison indicates that the value of the cumulative sample-to-sample carryover contribution is greater than the sensitivity threshold for the individual assay, step 170 of the algorithm 100 is encountered. At step 170, a determination is made as to whether a waiting period will delay the running of a STAT sample. If, for a given rerun assay or reflex test, the creation of a waiting period will delay the running of a STAT sample, then an additional sample container for the STAT sample is prepared at step 140, which step 140 is the same as the step 140 described previously. If, for a given rerun assay or reflex test, the creation of a waiting period will not delay the running of a STAT sample, at least one waiting period can be established at step 180. After the waiting period(s) are established, the algorithm 100 is completed, and the order of execution of assays is then established at step 190. At this point, the algorithm is complete (step 200) and the set of assays for a given sample can be carried out.

During a waiting period, a sample container is held, to prevent additional aspirations from the sample container, until the results from the assay in progress, which has used the sample from the original sample container, are reported. If a waiting period is not required, the order of execution of the assays is then established at step 190. At this point, the algorithm is complete (step 200) and the set of assays for a given sample can be carried out.

If a STAT sample is not required, and results are not required quickly, it could be cost-effective to have a sample held in a waiting period mode until results of an initial assay for that sample are reported (to receive an indication that a rerun assay or reflex test is or is not required) before continuing the order of execution of assays. In addition, if the device for dispensing the additional sample is occupied or located in a remote location, it may also be more expedient to wait until results are reported.

TABLE 5 illustrates the prioritization of a set of assays for a given sample, a sample-to-sample carryover calculation, an order for performing assays on a sample, and waiting periods to avoid receiving an ERROR MESSAGE on account of the performance of a rerun assay or a reflex test. For example, if an individual assay typically calls for a rerun assay or a reflex test, the algorithm can further include a subroutine that can call for the rerun assay or reflex test if the results of the individual assay fall into a range that normally calls for a rerun assay or reflex test. If the results of the individual assay fall outside of the range that normally calls for a rerun assay or reflex test, the sample is then released to continue the movement of the sample to another position in the system. TABLE 5 illustrates how the waiting period feature can be used to await the completion of an assay and then immediately monitor the results. This feature ensures that the value of the cumulative sample-to-sample carryover contribution does not increase excessively, with the result that a rerun assay can be performed without the need for aspirating at least one portion of a sample from the original sample container and dispensing that at least one portion into at least one additional sample container.

TABLE 5

| Order of assay from most sensitive to least sensitive | Sample-to-sample carryover contribution of each analyzer | | Cumulative sample-to-sample carryover contribution from the analyzers listed/requirement of additional sample container | |
| --- | --- | --- | --- | --- |
| A-5 | 0.1 ppm ($1 \times 10^{-7}$) | IA-3 | 0.1 ppm or $1 \times 10^{-7}$ | 0 | Additional sample container not required |
| WAIT for results. If the results of assay A-1 indicate that a retest is required, the sample is retested. If the results of assay A-1 indicate that a retest is not required, the sample is released to continue the movement of the sample. | | | | | |
| A-4 | 0.5 ppm ($5 \times 10^{-7}$) | IA-3 | 0.1 ppm ($1 \times 10^{-7}$) | 0.2 ppm[1] ($2 \times 10^{-7}$) | Additional sample container not required |

TABLE 5-continued

| Order of assay from most sensitive to least sensitive | | Sample-to-sample carryover contribution of each analyzer | | Cumulative sample-to-sample carryover contribution from the analyzers listed/requirement of additional sample container | |
|---|---|---|---|---|---|
| A-3 | 10 ppm $(1 \times 10^{-5})$ | IA-3 | 0.1 ppm $(1 \times 10^{-7})$ | 0.2 ppm[1] $(2 \times 10^{-7})$ | Additional sample container not required |
| A-1 | 100 ppm $(1 \times 10^{-4})$ | IA-2 | 0.1 ppm $(1 \times 10^{-7})$ | 0.3 ppm[1] $(3 \times 10^{-7})$ | Additional sample container not required |
| A-2 | 150 ppm $(1.5 \times 10^{-4})$ | IA-2 | 0.1 ppm $(1 \times 10^{-7})$ | 0.3 ppm[1] $(3 \times 10^{-7})$ | Additional sample container not required |

[1]Value of cumulative sample-to-sample carryover contribution is based on the situation where a rerun assay is required, and an assay from a different sample is run on analyzer IA-3 during the waiting period.

The algorithm 100 for the laboratory automation system will minimize the need for aspirating at least one portion of a sample from the original sample container and dispensing that at least one portion into at least one additional sample container. As a result, the number of operations performed on a dispensing device would be minimized, and additional sample containers and container-identifying indicia, such as, for example, barcodes, would also be minimized. The benefit of these savings would be lower cost per test for a laboratory and a reduction in the time for a result to be given to a doctor and/or a patient. More specifically, the elimination of dispensing devices reduces the cost of original equipment. In addition, the cost of an additional sample container and a label therefor is roughly equal to that of the original sample container. Accordingly, a second sample container for a given sample will double the variable costs of a set of assays. A second additional and a third additional sample container will triple the variable costs of a set of assays. In a high volume laboratory, one that processes approximately 1000 samples per day, the cost of additional sample containers can greatly add to the variable costs of the laboratory.

While the method has been described for use with laboratory automation systems and automated clinical analyzers, the method can be used in non-automated laboratory systems, in which an operator is provided with manual instructions for moving the sample container. The benefits of this manual process would be the same as described previously for the automated laboratory system.

In order to utilize the algorithm, only two classes of information need be known, namely (a) contribution of sample-to-sample carryover attributable to particular analyzers that aspirate the sample and (b) sensitivity thresholds attributable to particular assays. Because different assays typically have different sensitivity thresholds, these sensitivity thresholds need to be known for each assay in order to carry out the method of this invention.

In order to facilitate avoidance of contamination resulting from sample-to-sample carryover for sensitive assays, the order of execution of the assays is preferably arranged in the order of most sensitive assay to least sensitive assay. Then the arrangement thus determined is matched to the cumulative sample-to-sample carryover parameter, which is a function of the contributions of the probes of each analyzer in the laboratory system. In preferred embodiments, the method, or algorithm, described herein, is used in a laboratory automation system.

The following example illustrates the method described herein with commercially available assays and commercially available clinical analyzers.

EXAMPLE

In this example, the assays to be considered include those set forth in TABLE 6.

TABLE 6

| Assay | Name of assay (Abbreviation of assay) |
|---|---|
| Architect ® HbsAg: 34-4300/R2, Abbott Laboratories, Abbott Park, IL, September 2006 | Hepatitis B surface antigen (HBsAg) |
| Architect ® B12: 34-4080/R3, Abbott Laboratories, Abbott Park, IL, March 2006 | Vitamin B12 (B12) |
| Architect ® TSH: 34-3493/R6, Abbott Laboratories, Abbott Park, IL, February 2005 | Human thyroid stimulating hormone (TSH) |
| Architect ®/Aeroset ® Creatine Kinase, 30-3938/R4, Abbott Laboratories, Abbott Park, IL, January 2007 | Creatine kinase (CK) |
| Aeroset ®/Architect ® c8000 Glucose; 30-3085/R3, Abbott Laboratories, Abbott Park, IL, January 2003 | Glucose (Glu) |

In this example, the clinical analyzers to be considered include those set forth in TABLE 7.

TABLE 7

| Analyzer (Abbreviation of analyzer)[1] | Type of assay performed by analyzer[1] |
|---|---|
| Architect ® i2000, Abbott Laboratories, Abbott Park, IL (i2000) | Immunoassays |
| Architect ® i2000sr, Abbott Laboratories, Abbott Park, IL (i2000sr) | Immunoassays (also has STAT sample processing capability, denoted by the letter "s", and retest processing capability, denoted by the letter "r") |
| Architect ® c8000, Abbott Laboratories, Abbott Park, IL (c8000) | Photometric assays (absorbance assays) and Ion Specific Electrode/Integrated Chip Technology tests, both of which are considered to be "clinical chemistry" tests |
| Architect ® c16000, Abbott Laboratories, Abbott Park, IL (c16000) | Architect ® c16000 analyzer runs the same assay menu as does the Architect ® c8000 analyzer, but can perform twice as many tests/hour (1600 versus 800) |
| Aeroset ®, Abbott Laboratories, Abbott Park, IL | Aeroset ® analyzer is very similar to the Architect ® c16000 analyzer (and runs the same assays), but does not interface with any Architect ® |

TABLE 7-continued

| Analyzer (Abbreviation of analyzer)[1] | Type of assay performed by analyzer[1] |
|---|---|
| | analyzers, whereas the Architect ® i2000sr, i2000, and c8000 analyzers can be integrated with one another |

[1]If the model number of the instrument is preceded by the letter "i", the instrument performs immunoassays. Instruments listed in the foregoing table wherein the model number is preceded by the letter "i" utilize chemiluminescent microparticle immunoassay (CMIA) technology. If the model number of the instrument is preceded by the letter "c", the instrument performs clinical chemistry assays. Instruments listed in the foregoing table wherein the model number is preceded by the letter "c" utilize photometric (absorbance) and potentiometric technology. Two types of assay systems can be integrated, in which case the instrument can be labeled accordingly (e.g., ci8200 would be a c8000 analyzer integrated with an i2000 analyzer).

The following United States patents, incorporated herein by reference, are relevant to the ARCHITECT® clinical chemistry systems or their components:

U.S. Pat. Nos. 4,533,457; 4,619,739; 4,647,362; 4,678,755; 4,797,192; 5,025,389; 5,413,770

The following United States patents, incorporated herein by reference, are relevant to ARCHITECT® immunoassay systems or their components:

U.S. Pat. Nos. 5,468,646; 5,536,049; 5,543,524; 5,545,739; 5,565,570; 5,669,819; 5,682,662; 5,723,795; 5,795,784; 5,783,699; 5,856,194; 5,859,429; 5,915,282; 5,915,583; 5,938,120; 5,965,828; 6,022,746; 6,063,634; 6,150,113; 6,153,377; 6,162,645; 6,413,780; 6,562,298; 6,588,625

In this example, the sample-to-sample carryover for a single aspiration for the particular clinical analyzer listed is shown in TABLE 8.

TABLE 8

| Analyzer | Sample-to-sample carryover for a single aspiration |
|---|---|
| Architect ® i2000, Abbott Laboratories, Abbott Park, IL | 0.1 ppm ($1 \times 10^{-7}$) |
| Aeroset ®, Abbott Laboratories, Abbott Park, IL | 0.5 ppm ($5 \times 10^{-7}$) |
| Architect ® c8000, Abbott Laboratories, Abbott Park, IL | 0.1 ppm ($1 \times 10^{-7}$) |
| Architect ® i2000sr, Abbott Laboratories, Abbott Park, IL | 0.1 ppm ($1 \times 10^{-7}$) |
| Architect ® c16000, Abbott Laboratories, Abbott Park, IL | 0.1 ppm ($1 \times 10^{-7}$) |

In this example, the sensitivity thresholds for the assays to be carried out are set forth in TABLE 9.

TABLE 9

| Assay | Sensitivity threshold |
|---|---|
| CK | 100 ppm ($1 \times 10^{-4}$) |
| Glu | 150 ppm ($1.5 \times 10^{-4}$) |
| TSH | 10 ppm ($1 \times 10^{-5}$) |
| B12 | 0.5 ppm ($5 \times 10^{-7}$) |
| HbsAg | 0.1 ppm ($1 \times 10^{-7}$) |

In this example, the cumulative sample-to-sample carryover as a function of both order of assay from most sensitive to least sensitive and contribution to sample-to-sample carryover from the particular clinical analyzer that is expected to perform an individual assay is set forth in TABLE 10.

TABLE 10

| Order of assay from most sensitive to least sensitive | | Sample-to-sample carryover contribution of each analyzer | | Cumulative sample-to-sample carryover contribution from the analyzers listed/ requirement of additional sample container |
|---|---|---|---|---|
| HBsAg | 0.1 ppm ($1 \times 10^{-7}$) | i2000sr | 0.1 ppm ($1 \times 10^{-7}$) | 0 Additional sample container not required |
| B12 | 0.5 ppm ($5 \times 10^{-7}$) | i2000sr | 0.1 ppm ($1 \times 10^{-7}$) | 0.1 ppm ($1 \times 10^{-7}$) Additional sample container not required |
| TSH | 10 ppm ($1 \times 10^{-5}$) | i2000sr | 0.1 ppm ($1 \times 10^{-7}$) | 0.1 ppm ($1 \times 10^{-7}$) Additional sample container not required |
| CK | 100 ppm ($1 \times 10^{-4}$) | c8000 | 0.1 ppm ($1 \times 10^{-7}$) | 0.2 ppm ($2 \times 10^{-7}$) Additional sample container not required |
| Glu | 150 ppm ($1.5 \times 10^{-4}$) | c8000 | 0.1 ppm ($1 \times 10^{-7}$) | 0.2 ppm ($2 \times 10^{-7}$) Additional sample container not required |

In this example, the cumulative sample-to-sample carryover as a function of both order of assay from most sensitive to least sensitive and contribution to sample-to-sample carryover by the particular clinical analyzer that is expected to perform an individual assay is set forth in TABLE 11. However, TABLE 11 shows how a rerun assay or a retest for HbsAg would be indicated by the algorithm for ordering the execution of assays for a sample.

TABLE 11

| Order of assay from most sensitive to least sensitive | | Sample-to-sample carryover contribution of each analyzer | | Cumulative sample-to-sample carryover contribution from the analyzers listed/ requirement of additional sample container |
|---|---|---|---|---|
| HbsAg | 0.1 ppm ($1 \times 10^{-7}$) | i2000sr | 0.1 ppm ($1 \times 10^{-7}$) | 0 Additional sample container not required |
| B12 | 0.5 ppm ($5 \times 10^{-7}$) | i2000sr | 0.1 ppm ($1 \times 10^{-7}$) | 0.1 ppm ($1 \times 10^{-7}$) Additional sample container not required |

TABLE 11-continued

| Order of assay from most sensitive to least sensitive | Sample-to-sample carryover contribution of each analyzer | | | Cumulative sample-to-sample carryover contribution from the analyzers listed/ requirement of additional sample container | |
|---|---|---|---|---|---|
| TSH | 10 ppm $(1 \times 10^{-5})$ | i2000sr | 0.1 ppm $(1 \times 10^{-7})$ | 0.1 ppm $(1 \times 10^{-7})$ | Additional sample container not required |
| CK | 100 ppm $(1 \times 10^{-4})$ | c8000 | 0.1 ppm $(1 \times 10^{-7})$ | 0.2 ppm $(2 \times 10^{-7})$ | Additional sample container not required |
| Glu | 150 ppm $(1.5 \times 10^{-4})$ | c8000 | 0.1 ppm $(1 \times 10^{-7})$ | 0.2 ppm $(2 \times 10^{-7})$ | Additional sample container not required |
| Rerun HBsAg | 0.1 ppm $(1 \times 10^{-7})$ | i2000sr | 0.1 ppm $(1 \times 10^{-7})$ | 0.3 ppm $(3 \times 10^{-7})$ | ERROR MESSAGE |

In this example, the cumulative sample-to-sample carryover as a function of both order of assay from most sensitive to least sensitive and carryover contribution from each analyzer is set forth in TABLE 12. However, TABLE 12 shows how a waiting period for HBsAg would enable retesting of HBsAg without giving an ERROR MESSAGE.

TABLE 12

| Order of assay from most sensitive to least sensitive | Sample-to-sample carryover contribution of each analyzer | | | Cumulative sample-to-sample carryover contribution from the analyzers listed/ requirement of additional sample container | |
|---|---|---|---|---|---|
| HBsAG | 0.1 ppm $(1 \times 10^{-7})$ | i2000sr (1) | 0.1 ppm $(1 \times 10^{-7})$ | 0 | Additional sample container not required |
| WAIT for results. If the results of assay A-1 indicate that a retest is required, the sample is retested. If the results of assay A-1 indicate that a retest is not required, the sample is released to continue the movement of the sample. | | | | | |
| B12 | 0.5 ppm $(5 \times 10^{-7})$ | i2000sr (2) | 0.1 ppm $(1 \times 10^{-7})$ | 0.1 ppm $(1 \times 10^{-7})$ | Additional sample container not required |
| TSH | 10 ppm $(1 \times 10^{-5})$ | i2000sr (2) | 0.1 ppm $(1 \times 10^{-7})$ | 0.1 ppm $(1 \times 10^{-7})$ | Additional sample container not required |
| CK | 100 ppm $(1 \times 10^{-4})$ | c8000 (1) | 0.1 ppm $(1 \times 10^{-7})$ | 0.2 ppm $(2 \times 10^{-7})$ | Additional sample container not required |
| Glu | 150 ppm $(1.5 \times 10^{-4})$ | c8000 (1) | 0.1 ppm $(1 \times 10^{-7})$ | 0.2 ppm $(2 \times 10^{-7})$ | Additional sample container not required |

In this example, the sample is held after the HbsAG assay is started on the i2000sr analyzer. Two possible courses of action could result.

(a) The result of the HbsAG assay is within range, and a rerun assay is not required. The sample is then released to continue the movement of the sample.

(b) The result of the HBsAG assay is not within range, or the result of the HbsAG assay is unexpected and a rerun assay is required. The sample is sent to the same i2000sr analyzer for another HBsAG test, and then released to continue the movement of the sample. In this example, the sample is not held for a second time to await results from the rerun assay.

The algorithm of the laboratory automation system will minimize the need for transferring samples from the original sample container to an additional sample container. As a result, the number of operations typically performed with disposable tips on an aspiration/dispensing probe would be greatly reduced, thereby reducing the costs of disposable items, and the need for additional sample containers (e.g., sample tubes) and container-identifying indicia (e.g., barcodes) would also be eliminated, thereby further reducing the costs of disposable items. The results of these savings would lead to lower cost per assay or test for a laboratory, and reduced time for reporting results to the doctor and/or the patient. The algorithm reduces the potential for interference caused by sample-to-sample carryover into a given sample, thereby resulting in maintaining the integrity of the given sample and the accuracy and precision of the test results for the given sample.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for arranging assays in an order for execution in a system that employs a plurality of clinical analyzers and carrying out said assays after said assays are arranged in said order for execution, said method comprising the steps of:

(a) prioritizing the order of execution of a number of individual assays in a set of assays for a given sample in an original sample container, the priority of an individual assay in the set of assays for the given sample being specified by the sensitivity of the individual assay, wherein there is at least one sample-to-sample carryover contribution from at least one other sample, an assay of the at least one other sample preceding the individual assay of the given sample;

(b) calculating the sum of the sample-to-sample carryover contribution(s) from the at least one other sample for at least one assay of the at least one other sample that precedes the individual assay of the given sample;

(c) comparing the sum calculated in step (b) to the sensitivity threshold of the individual assay of the given sample; and (d) if the sum calculated in step (b) is less than the sensitivity threshold of the individual assay of the given sample, establishing an order for execution of assays for the given sample that includes the individual assay of the given sample;

(e) carrying out the individual assays in the order established in step (d); but (f) if the sum calculated in step (b) is greater than the sensitivity threshold of the individual assay of the given sample, aspirating at least one portion of the given sample from the original sample container and dispensing that at least one portion into at least one additional sample container, the at least one portion of the given sample dispensed into the at least one additional sample container to be used to carry out the individual assay of the given sample;

(g) carrying out the individual assays in the order established in step (f).

2. The method of claim 1, further including the step of determining sample-to-sample carryover values by taking account of additional rerun assays and/or reflex tests prior to establishing the order for execution of assays.

3. The method of claim 2, further including the step of calculating the sum of sample-to-sample carryover values of each of the assays of the plurality of assays that include the individual assay of the given sample and calculating the sum of sample-to-sample carryover values for the additional rerun assays and/or reflex tests.

4. The method of claim 2 wherein (a) the sum of sample-to-sample carryover values of each of the assays of the plurality of assays that provide the individual assay of the given sample plus the sum of sample-to-sample carryover values for the additional rerun assays and/or reflex tests is compared with the sensitivity threshold of the individual assay of the given sample, and if the plurality of sums calculated in step (a) is greater than the sensitivity threshold of the individual assay of the given sample, a determination is made as to whether a waiting period will delay the assay of a STAT sample, but if the sum calculated in step (a) is less than the sensitivity threshold of the individual assay of the given sample, establishing an order for execution of assays that includes the individual assay of the given sample and the assays preceding the individual assay of the given sample.

5. The method of claim 4, wherein if a waiting period delays the assay of a STAT sample, dispensing at least one portion of the sample into at least one additional sample container, the at least one additional portion being used to carry out the individual assay of the given sample, but if the waiting period will not delay the assay of a STAT sample, establishing a waiting period for an assay result.

6. The method of claim 5, further including the step of establishing an order for the execution of assays after the waiting period is established.

* * * * *

UNITED STATES PATENT AND TRADEMARK OFFICE
CERTIFICATE OF CORRECTION

| | |
|---|---|
| PATENT NO. | : 8,112,229 B2 |
| APPLICATION NO. | : 11/809256 |
| DATED | : February 7, 2012 |
| INVENTOR(S) | : Patrick P. Fritchie and John Curtis Jones |

It is certified that error appears in the above-identified patent and that said Letters Patent is hereby corrected as shown below:

On the Title Page

Item (56) OTHER PUBLICATIONS section on Page 2, insert the reference:

-- R. Haeckel, International Union of Pure and Applied Chemistry - Proposals for the Description and Measurement of Carry-Over Effects in Clinical Chemistry, 63 PURE & APPL. CHEM. 301-306 (1991). --

Signed and Sealed this
Twenty-seventh Day of August, 2013

Teresa Stanek Rea
*Acting Director of the United States Patent and Trademark Office*